US012458403B1

(12) United States Patent
Groop

(10) Patent No.: US 12,458,403 B1
(45) Date of Patent: Nov. 4, 2025

(54) HYDRO DERMABRASION DEVICE WITH MICRONEEDLES

(71) Applicant: Lawrence G Groop, Two Harbors, MN (US)

(72) Inventor: Lawrence G Groop, Two Harbors, MN (US)

( * ) Notice: Subject to any disclaimer, the term of this patent is extended or adjusted under 35 U.S.C. 154(b) by 0 days.

(21) Appl. No.: 19/026,053

(22) Filed: Jan. 16, 2025

(51) Int. Cl.

| | |
|---|---|
| ***A61M 35/00*** | (2006.01) |
| ***A61B 17/50*** | (2006.01) |
| *A61B 17/00* | (2006.01) |

(52) U.S. Cl.
CPC .... *A61B 17/50* (2013.01); *A61B 2017/00539* (2013.01); *A61B 2017/00761* (2013.01); *A61B 2217/005* (2013.01)

(58) Field of Classification Search
CPC .......... A61B 17/50; A61B 2017/00761; A61B 2017/00539; A61B 2217/005
See application file for complete search history.

(56) References Cited

U.S. PATENT DOCUMENTS

| | | | | |
|---|---|---|---|---|
| 10,967,163 | B1 * | 4/2021 | Groop | A61M 37/0015 |
| 2013/0197550 | A1 * | 8/2013 | Dietz | G10K 11/24 156/60 |
| 2018/0303515 | A1 * | 10/2018 | Shadduck | A61B 17/320068 |
| 2019/0133642 | A1 * | 5/2019 | Ignon | A61B 17/54 |

* cited by examiner

*Primary Examiner* — Anh T Dang
(74) *Attorney, Agent, or Firm* — Hartman Titus PLC; Joseph W Mott

(57) ABSTRACT

An applicator tip for the hand piece of a hydro dermabrasion device is disclosed. Treatment fluid supply and suction lines are integrated with a retractable microneedle array.

2 Claims, 6 Drawing Sheets

HYDRO DERMABRASION DEVICE WITH MICRONEEDLES

TECHNICAL FIELD OF THE INVENTION

The disclosed device relates to the application of solutions from a device with a motorized pump, handpiece, and specialized tip with the intent of exfoliating the skin while simultaneously incorporating an array of microneedles in this tip to assist in the exfoliation. Further embodiments include components that enhance the comfort and efficiency of the exfoliation.

BACKGROUND OF THE INVENTION

Currently, clinicians use "hydro dermabrasion" as a method of exfoliating and beautifying the skin. The apparatus includes at least two motorized pump units with fluid solution reservoirs, a hose that connects the supply and suction pumps to a handpiece, and a single use "tip" attachment that has tubes through it (connected to the supply pump tube and reservoir). One tube allows fluid to enter the tip and express onto the skin on one side of the tip via an aperture. On the other side of tip is another tube and aperture that allows fluids and skin cell remnants to be suctioned away from the surface of the skin into the suction tube that is connected to the suction pump that stores the spent fluid into a reservoir inside the machine.

Another method of exfoliating the skin is to use metal microneedles arranged on an array and then moving the array around the skin which allows the needles to exfoliate the top layer of the epidermis-stratum corneum. It is necessary to use a "glide serum" or whetting agent to reduce the friction that the microneedle array has when held perpendicular and moved across the surface of the skin.

SUMMARY OF THE DISCLOSURE

This invention combines both exfoliation technologies into one single-use "tip" attachment to the handpiece. It leverages the liquid exfoliant solution to also act as a glide serum for the motion of the perpendicular tip across the surface of the skin.

An applicator assembly attaches to a hydro dermabrasion handpiece, which may be of different designs and configurations, with two lumens that align with supply and suction lumens on the handpiece interface. The lumens pass through the applicator tip to two apertures (supply and suction) on the surface of a protective plate through which, when the clinician pushes down on the handpiece, microneedles emerge through guide holes in a protective plate and assist in the exfoliation of the skin. This sequence can occur by itself or simultaneously with the expression and suction of the exfoliation solution of the hydro dermabrasion device.

In one embodiment, an applicator tip attaches to the handpiece interface by either threaded or bayonet insertion design. The applicator assembly allows fluid to be expressed onto the skin via the supply lumen and subsequently suctioned away from the skin through the return suction lumen, independent of the advancement or retraction of the microneedle array through the protective plate. A spring mechanism prevents the microneedle array from advancing through the protective plate without the downward, intentional pressure of the applicator tip against the skin. When the procedure is finished, the applicator tip is detached from the hydro dermabrasion handpiece and discarded.

DETAILED DESCRIPTION

Figure 1:
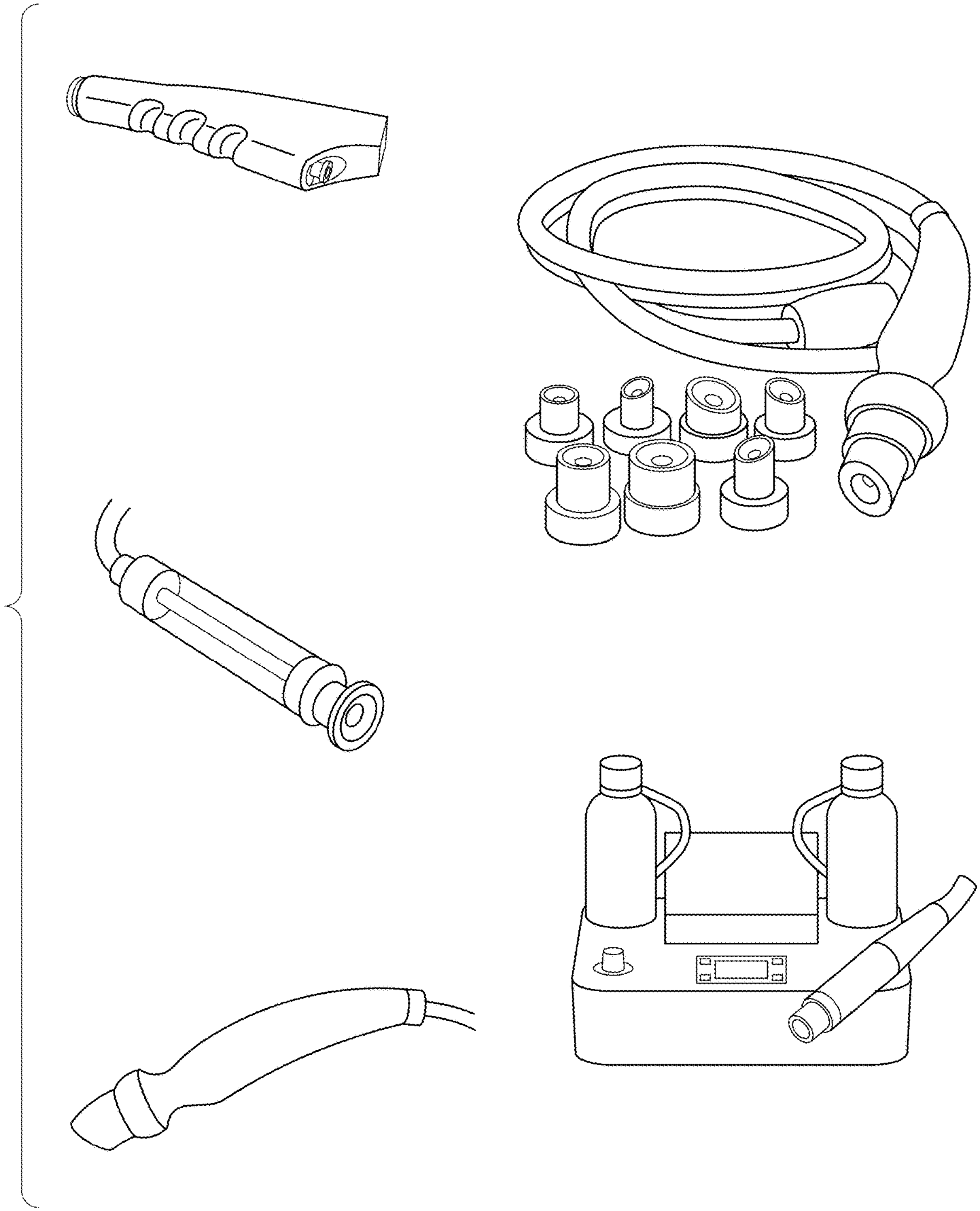
FIG. 1 shows different embodiments of handpieces for use with hydro dermabrasion devices.
Figure 2:
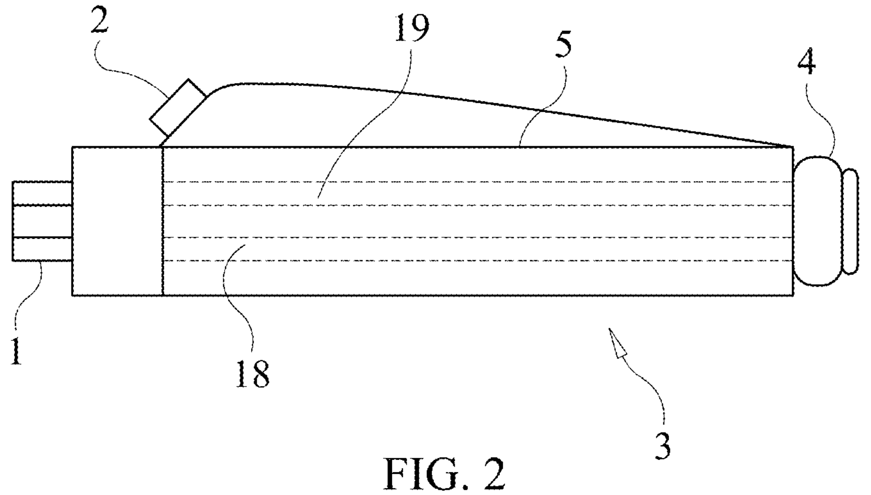
FIG. 2 shows a version of a handpiece for use with the current invention.
Figure 3:
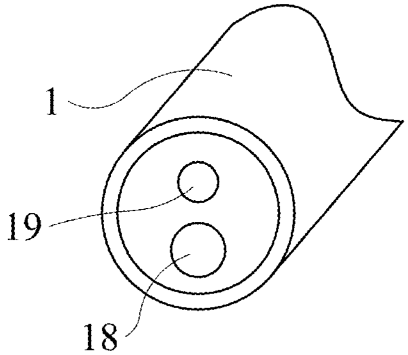
FIG. 3 shows a proximal end view of the handpiece of FIG. 2.
Figure 4:
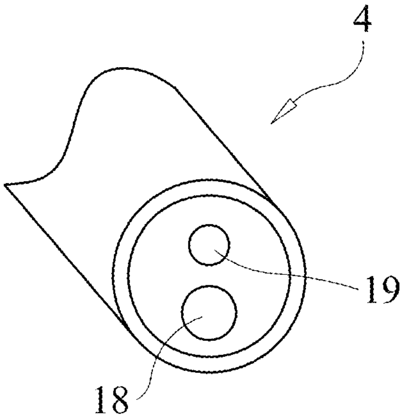
FIG. 4 shows a distal end view of the handpiece of FIG. 2.
Figure 5:
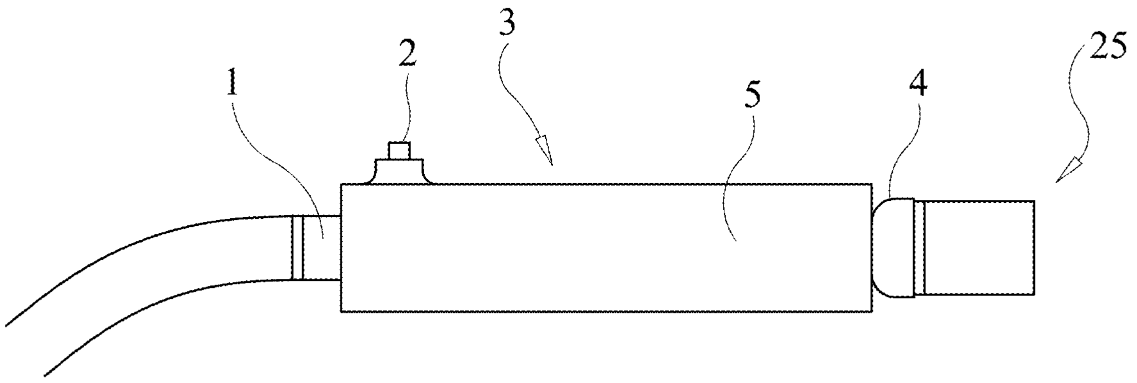
FIG. 5 shows a handpiece with an embodiment of the current invention attached.

To provide a more complete understanding of the present invention and features and advantages thereof, reference is made to the following description, taken in conjunction with the accompanying figures, wherein like reference numerals represent like parts.

Figure 9:
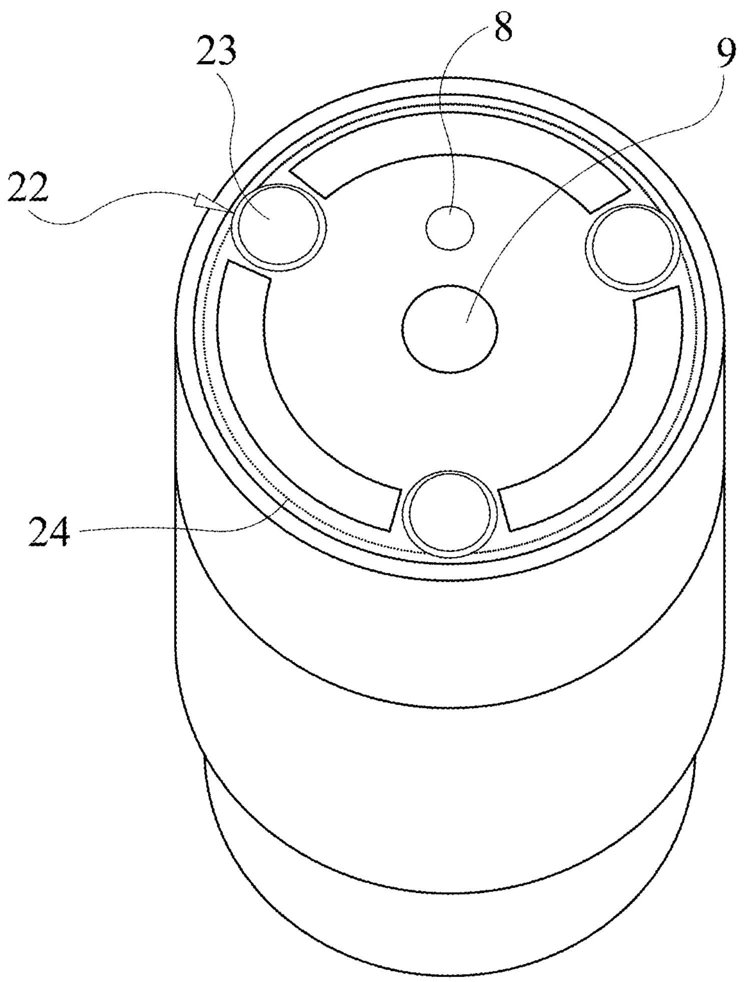
FIG. 9 shows an end view of the embodiment of FIG. 7.

As seen in FIGS. 2-5, a hydro dermabrasion handpiece 3, to which the current invention attaches, comprises an elongated body 5 with a suction/supply hose interface 1 on its proximal end and a handpiece applicator tip interface 4 on its distal end. Interface 1 incorporates openings at the end of lumens that connect to a solution supply 19 and a suction tube 18 from the main hydro dermabrasion machine (not shown). Tubes 18 and 19 pass through the body 5 and emerge at the applicator tip interface 4, where they align with tubes or apertures in the applicator tip. In an embodiment of the current invention, tubes 18 and 19 align with suction lumen 6 and solution supply lumen 13, respectively, of applicator tip assembly 25 (FIGS. 5 & 7) and with distal openings 8 and 9 (FIG. 9). In the illustrated embodiment, the solution supply line 18,13,9 is near the central axis of the tip 25 and the suction line 19,6,8 is off to the side. This configuration helps more evenly distribute the solution along the skin. Other configurations, which may include more than one suction or supply line through the tip, may be deployed.

A dual pump actuation trigger 2, which turns on the vacuum pump and the liquid supply pump of the hydro dermabrasion machine, is preferably integral with the handpiece, although a switch on the machine may perform this function.

Figure 6:
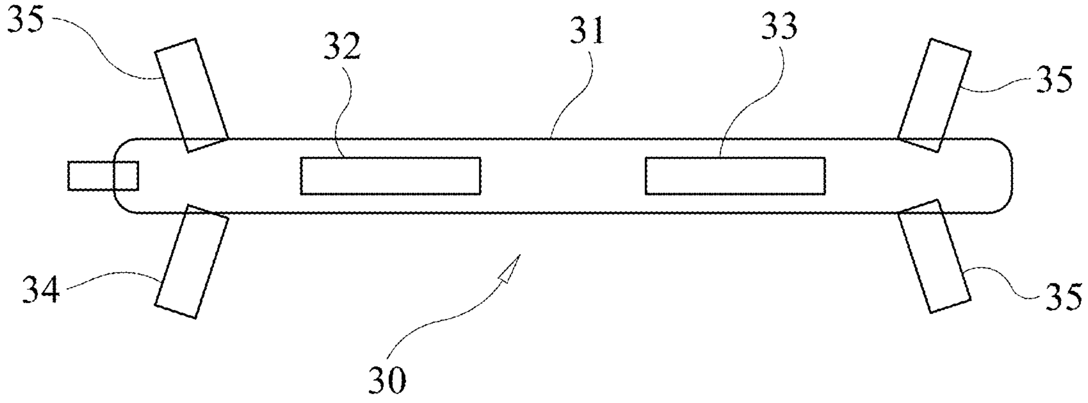
FIG. 6 shows an embodiment of an external vibration unit that may be attached to a handpiece for use with the current invention.

When using a hydro dermabrasion handpiece 3 with an embodiment of the current invention, it may be advantageous to apply vibrations to the handpiece. FIG. 6 shows a schematic embodiment of an external vibration unit 30 adaptable to the handpiece, comprising a main body cylinder 31 with a power supply (such as a battery) 32 and a vibration motor 33 and an on/off switch 34. Attachment tabs 35 may permanently or removably affix the vibrator to the handpiece.

Figure 7:
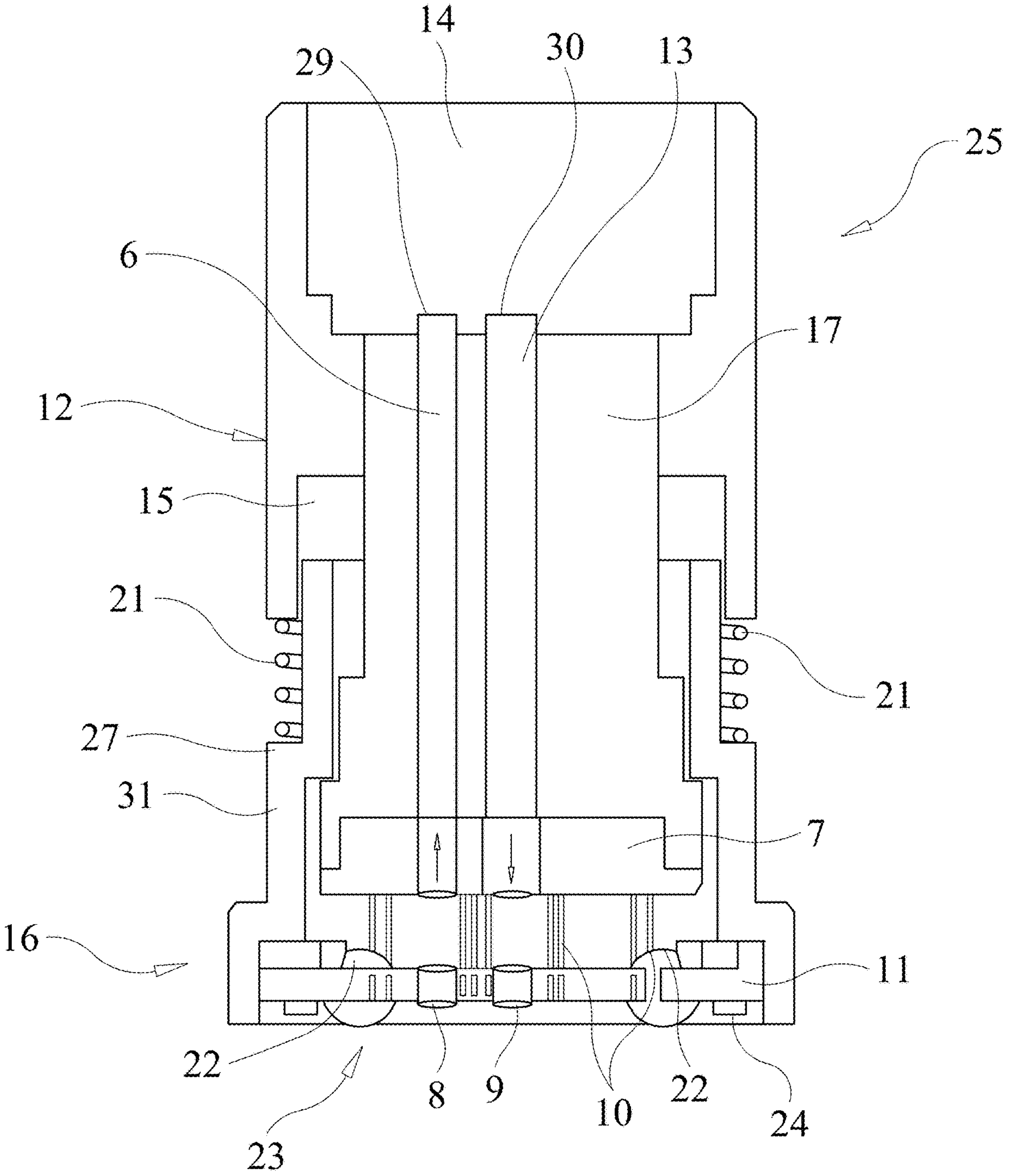
FIG. 7 shows a cut away view of an embodiment of the current invention.
Figure 8:
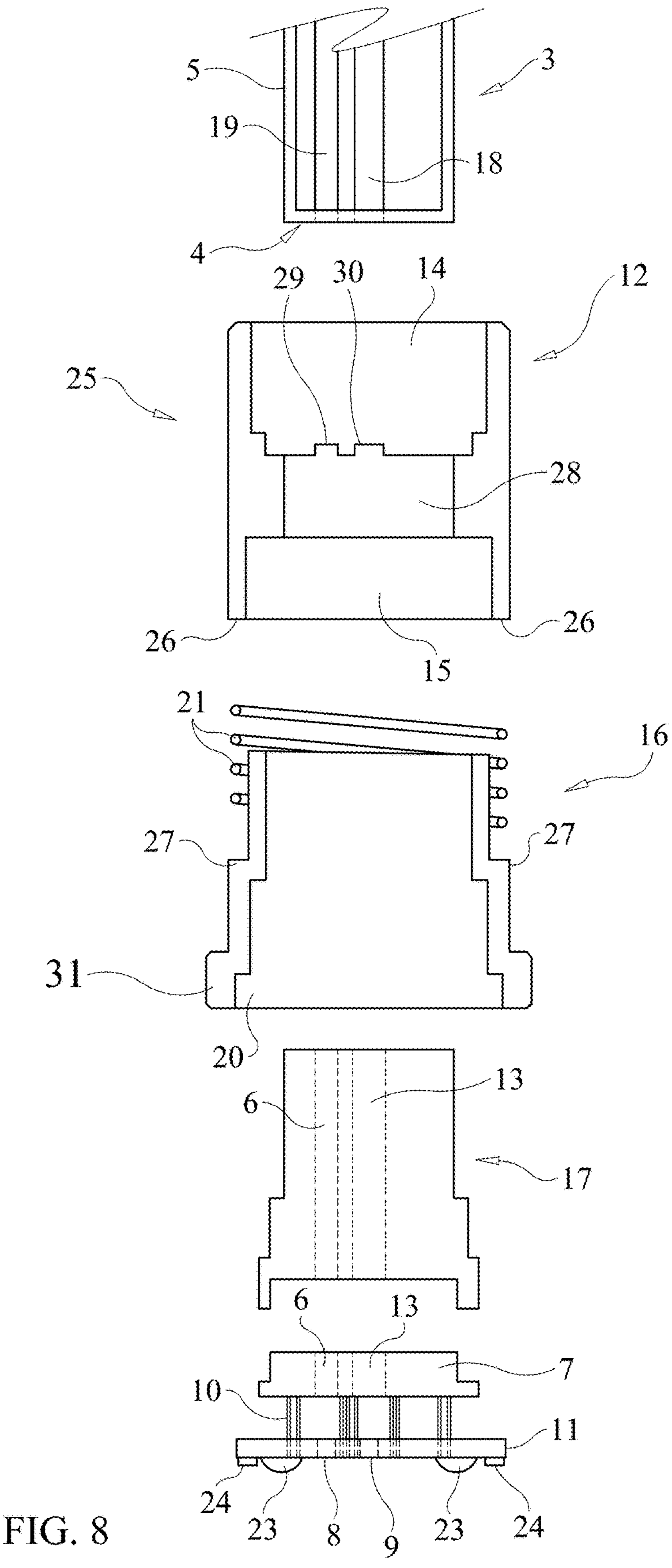
FIG. 8 shows an exploded cut away view of the embodiment of FIG. 7.

As shown in FIGS. 7-9, single-use applicator tip assembly 25 includes an upper cylinder body 12, a lower cylinder body 16 and a needle array base holder 17. The upper cylinder body 12 has an upper chamber 14 dimensioned to releasably attach to the handpiece 3. When the handpiece 3 is in position, the tip interface 4 aligns a solution supply tube 18 and a suction tube 19 with corresponding solution supply 30 and suction 29 interfaces in the upper cylinder body 12. In the illustrated embodiment, supply interface 30 and suction interface 29 extend upward and are inserted into the supply 19 and suction 19 tubes in tip interface 4. Other connections are possible to align the respective tubes. For example, tip interface 4 could have extensions of its tubes that fit into the tubes in upper cylinder body 12.

Upper cylinder body 12 also has a lower chamber 15 dimensioned to movably engage lower cylinder body 16. A spring 21 is positioned between the lower wall 26 of upper cylinder body 12 and an external ledge 27 around the lower cylinder body 16 so that downward movement of the upper cylinder body relative to the lower cylinder body compresses the spring. The spring may be fixedly attached, with glue or another method, to the lower wall 26 and the ledge 27 in order to prevent separation of the upper cylinder body from the lower cylinder body. The chamber 20 of the lower cylinder body 16 is configured to slidably contain a needle array base holder 17.

Needle array base holder 17 is a solid cylinder with a solution supply lumen 13 and a suction lumen 6. The upper end of the holder 17 is fixedly attached to the upper cylinder body 12 with its suction and supply lumens aligned with the corresponding lumens in the upper cylinder body. A needle array base 7 is attached to a chamber in the bottom of the holder. Solution supply 13 and suction 6 lumens in the array base align with corresponding lumens 13 and 6 in the holder 17. A plurality of microneedles 10 extend downward from the array base 7.

Protective plate 11 attaches inside the lower end of the cavity 20 in the lower cylinder body 16 and forms the bottom of the tip assembly 25. Openings in the plate 11 are positioned to allow microneedles 10 to pass through, and larger openings 8 and 9 align with the suction 6 and solution supply 13 lumens in the array base 17.

FIG. 9 is a bottom view of applicator tip assembly 25. A plurality of ball bearings 23 are retained on protective plate 11 by means of ball bearing concavities 22 molded into the plate. The ball bearings 23 may be plastic, metal, glass or other material. A plurality of curved thermoplastic resin surface strips 24 protrude slightly from the protective plate 11.

In operation, the handpiece applicator tip interface 4 is inserted into the upper chamber 14 of the assembled applicator tip 15. Solution supply tube 18 and suction tube 19 align with solution lumen 13 and suction lumen 6 that run all the way through the apparatus to suction opening 8 and supply opening 9. The clinician activates the hydro dermabrasion machine and presses the applicator tip against the skin then pushes downward. Spring 21 is compressed by downward push of the hydro dermabrasion handpiece 3 toward the skin. Compression of spring 21 advances microneedle array base 7, which advances microneedles 10 past protective plate 11 and into the skin. When the clinician releases downward pressure, the spring decompresses, the needles retract, and the clinician shifts the tip to a new location. Using the trigger 2, the clinician may apply solution, suction, or both.

The ball bearings 23 reduce friction of the protective plate 11 against the skin while the needles are retracted. The surface strips 24 assist the liquid agent dispersion across the skin, and also help seal the cartridge against the skin to prevent suction loss and liquid leakage. If the clinician keeps the dual pump actuation trigger 2 depressed continuously, the suction function of the device will suction up the expressed solution and any skin cell remnants via suction aperture 8 in the assembly.

Once the clinician has completed the treatment, he/she simply detaches applicator tip assembly 15 from handpiece applicator tip interface 4 and disposes of the assembly.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Numerous other changes, substitutions, variations, alterations, and modifications may be ascertained to one skilled in the art. Therefore, it is intended that the invention not be limited to the particular embodiments disclosed for carrying out the invention.

The invention claimed is:

1. An applicator for use with a handpiece of a hydro dermabrasion device for treating skin, having solution supply and suction apertures, comprising:

- a cylinder that connects to the handpiece, comprising an upper cylinder body with upper and lower walls and a lower cylinder body;
  - the upper cylinder body comprising an upper chamber, a lower chamber and a connecting chamber;
  - wherein the upper chamber has an open top and a bottom with a supply aperture and a suction aperture and is removably attachable to the handpiece, and the lower chamber and connecting chamber are connected and each has an open bottom;
  - the lower cylinder body being dimensioned to slidably fit inside the lower chamber of the upper cylinder body;
- a microneedle array base holder, with a supply lumen and a suction lumen, directly attached to the bottom of the upper chamber of the upper cylinder body;
- a microneedle array base attached to the holder, having supply and suction lumens therethrough and a plurality of microneedles extending therefrom;
- a protective plate having apertures for the microneedles and supply and suction lumens therethrough, attached to the lower cylinder body below the microneedle array base; and
- a spring positioned between the lower wall of the upper cylinder body and a ledge around the lower cylinder body;
- wherein the supply aperture, the microneedle array base holder supply lumen, the microneedle array base supply lumen and the protective plate supply lumen are aligned to form a continuous solution supply path through the applicator, the suction aperture, the microneedle array base holder suction lumen, the microneedle array base suction lumen and the protective plate supply lumen form a continuous path through the applicator and the microneedles are reciprocally passable through the safety plate to the treated skin.

2. The applicator of claim 1 wherein the safety plate includes a plurality of ball bearing concavities with ball bearings and a plurality of raised surface strips along a periphery between the ball bearings.

* * * * *